US 6,639,235 B1

United States Patent
Gurgoze

(10) Patent No.: US 6,639,235 B1
(45) Date of Patent: Oct. 28, 2003

(54) APPARATUS FOR HOLDING AND TRANSPORTING MULTIPLE RADIATION MODULATING DEVICES AND METHOD THEREFOR

(76) Inventor: Erdal M. Gurgoze, 33236 N. 48th Pl., Cave Creek, AZ (US) 85331

( * ) Notice: Subject to any disclaimer, the term of this patent is extended or adjusted under 35 U.S.C. 154(b) by 0 days.

(21) Appl. No.: 10/227,397

(22) Filed: Aug. 23, 2002

(51) Int. Cl.[7] .................................................. G21F 5/02
(52) U.S. Cl. ............................... 250/498.1; 250/496.1; 250/503.1; 250/505.1; 378/65
(58) Field of Search ........................ 250/498.1, 497.1, 250/493.1, 503.1, 505.1, 515.1; 378/65; 600/1, 2

(56) References Cited

U.S. PATENT DOCUMENTS

| | | | | |
|---|---|---|---|---|
| 3,840,747 A | * | 10/1974 | Macovski | ................. 250/505.1 |
| 4,798,961 A | * | 1/1989 | Augustsson | ............... 250/515.1 |
| 4,933,813 A | * | 6/1990 | Berger | ............................ 362/2 |
| 5,162,655 A | * | 11/1992 | Peters | ...................... 250/498.1 |
| 6,191,428 B1 | * | 2/2001 | Gilberti | .................... 250/498.1 |
| 6,268,959 B1 | * | 7/2001 | Kawahito | .................... 359/391 |
| 2002/0180869 A1 | * | 12/2002 | Callison et al. | ............. 348/203 |
| 2003/0086527 A1 | * | 5/2003 | Speiser et al. | ................. 378/65 |

* cited by examiner

*Primary Examiner*—John R. Lee
*Assistant Examiner*—James P. Hughes
(74) *Attorney, Agent, or Firm*—Jeffrey D. Moy; Harry M. Weiss; Weiss, Moy & Harris, P.C.

(57) ABSTRACT

An apparatus for altering the radiation intensity delivered from a radiation source has a plate member for holding a plurality of radiation modulating devices. A frame member is coupled to the radiation source for holding the plate member between the radiation source and a target area. The frame member allows the plate member to rotate within the frame member so different radiation modulating devices may be positioned between the radiation source and the target area to alter the radiation intensity delivered.

11 Claims, 2 Drawing Sheets

APPARATUS FOR HOLDING AND TRANSPORTING MULTIPLE RADIATION MODULATING DEVICES AND METHOD THEREFOR

BACKGROUND OF THE INVENTION

1. Field of the Invention

This invention relates to a radiation devices, and more specifically, to an apparatus which is coupled to a radiation device which will allow the radiation device to alter the amount of radiation delivered to the body.

2. Description of the Prior Art

Cancer is the second leading cause of death in the U.S., exceeded only by heart disease. The American Cancer Society predicts that over 1.2 million new cancer cases would be diagnosed in the U.S. this year and that over 550,000 Americans would die of the disease. At this rate, approximately 1,500 Americans die each day of cancer.

In order to treat patients diagnosed with cancer, doctors generally have three alternatives: surgery, chemotherapy, and radiation therapy. These techniques are often used in combination with one another. Radiation therapy is generally used in treatment of nearly two-thirds of all cancer patients. In radiation therapy, high-energy rays are used to damage cancer cells and stop the cancer cells from growing and dividing. Thus, radiation therapy may stop the growth of a cancerous tumor and even destroy all the cells of the tumor. Where complete tumor destruction is not possible, radiation may be used to shrink a tumor, so that it can be more easily removed surgically. Radiation may also be used after surgery to destroy microscopic remnants of the cancer which were not removed during surgery.

Radiation therapy is generally used as a local treatment. In other words, radiation treatment is suppose to affect cancer cells only in the treated area. This is in contrast to chemotherapy. Chemotherapy kills cancer cells throughout the body and kills many healthy cells as well. While the goal of radiation therapy is to deliver radiation only to the treatment area, various limitations exists. For example, in treating prostrate cancer with external radiation therapy, the radiation beam may pass through portions of the skin, rectum, bladder, and genitalia, often causing inflamation and potentially serious damage to those tissues and organs.

To minimize these negative effects, it is important to deliver as much radiation to a target area as possible, while minimizing the amount of radiation delivered to surrounding healthy structures. Advances in radiation therapy techniques aid in this regard. One such technique is called "intensity modulated radiation therapy" ("IMRT"). As with most radiation therapy techniques, IMRT involves two stages—treatment planning and radiation delivery. Treatment planning involves examining the area of cancer in a patient via imaging studies, such as computed tomography studies ("CT scans") and/or magnetic resonance imaging ("MRI"). Typically, a clinician responsible for treatment planning, such as a radiation oncologist, then defines the optimal dose of radiation to be delivered to the treatment site and the tolerable level of radiation to be administered to the surrounding tissues. Sophisticated computer software processes the imaging information and clinician defined parameters to create a treatment plan. Another set of sophisticated software then translates the treatment plan into instructions for a radiation delivery device. A radiation delivery device used for IMRT typically includes a radiation accelerator, which creates a beam of radiation, and a radiation beam collimator (or multi-leaf collimator "MLC"), which blocks portions of the beam for specific time intervals. Both the accelerator and the MLC are typically controlled by instructions formulated by the computer software mentioned above.

The objective of IMRT is to partially block portions of a radiation beam that pass through important healthy bodily structures, to reduce radiation doses to those structures, while allowing as much of the radiation beam as possible to arrive at a cancerous target area. Treatment results have shown that this objective is being met. For example, IMRT has been used successfully over the past several years to treat prostate cancer while decreasing doses to the rectum and bladder, at such hospitals as Memorial Sloan Ketering Cancer Center.

While IMRT techniques provide a potentially revolutionary approach to radiation therapy, the vast majority of the clinics, hospitals, and other facilities that provide radiation therapy cannot afford the equipment to provide it. As healthcare cost increase throughout the world, healthcare providers must make difficult choices regarding how to provide the best possible services at prices their patients can afford. Although most clinicians would prefer to purchase every cutting edge medical technology available, they simply cannot afford to do so while still caring for their patients in an affordable manner.

The basic machinery needed to provide IMRT is a linear accelerator, an MLC, a computer system for controlling the accelerator and the MLC, and a computer system for creating treatment plans. Unfortunately, only about 10% of the currently used radiation therapy systems can be upgraded with these components to provide IMRT. Most currently used systems are typically incompatible because linear accelerators must be digital to be upgraded to provide IMRT, and most currently available systems use analog accelerators.

Unfortunately, most healthcare providers cannot afford a new IMRT radiation therapy system. Furthermore, it generally fairly expensive to upgrade to a digital radiation therapy system to provide IMRT.

A cheaper alternative to IMRT is to use a radiation modulating device for wholly or partially blocking one or more portions of a radiation beam. In this alternative, a radiation modulating device is positioned between a radiation source and a target area. The radiation beam will be blocked in such a manner as to vary the intensities across its field when it reaches a target. Thus, a radiation modulating device may be configured to specifically vary the intensities of a radiation beam to have a given effect on a target and/or on areas surrounding a target. For example, a radiation modulating device may be configured to allow a sufficient intensity of a radiation beam to be delivered to one area of a cancerous tumor, while limiting the intensity of the beam being delivered to a vital structure surrounding the tumor.

One problem with radiation modulating devices is that in order to alter the intensity of a radiation beam to be delivered to different patients, different radiation modulating devices must be positioned between the radiation source and the target area. This requires the removal of the current radiation modulating device, and the placement of a new radiation modulating device between the radiation source and the target area. Furthermore, to treat different areas of person's body, different radiation modulating devices must be positioned between the radiation source and the target area. This requires the stoppage of radiation treatment, the removal of the current radiation modulating device, and the placement of a new radiation modulating device between the radiation source and the target area.

Therefore, a need existed-to provide a device and method that enables conventional radiation therapy systems to be adapted to provide innovative therapy techniques in a cost effective, manner. The device and method must be able to over come the problems associated with prior art devices and methods.

SUMMARY OF THE INVENTION

In accordance with one embodiment of the present invention, it is an object of the present invention to provide a device and method that enables conventional radiation therapy systems to be adapted to provide innovative therapy techniques in a cost effective manner.

It is another object of the present invention to provide a device and method that enables conventional radiation therapy systems to be adapted to provide innovative therapy techniques in a cost effective manner that is able to over come the problems associated with prior art devices and methods.

BRIEF DESCRIPTION OF THE EMBODIMENTS

In accordance with one embodiment of the present invention an apparatus for altering the radiation intensity delivered from a radiation source is disclosed. The apparatus comprises a plate member for holding a plurality of radiation modulating devices. A frame member is coupled to the radiation source for holding the plate member between the radiation source and a target area. The frame member allows the plate member to rotate within the frame member so different radiation modulating devices may be positioned between the radiation source and the target area to alter the radiation intensity delivered.

The foregoing and other objects, features, and advantages of the invention will be apparent from the following, more particular, description of the preferred embodiments of the invention, as illustrated in the accompanying drawing.

BRIEF DESCRIPTION OF THE DRAWINGS

The novel features believed characteristic of the invention are set forth in the appended claims. The invention itself, as well as a preferred mode of use, and advantages thereof, will best be understood by reference to the following detailed description of illustrated embodiments when read in conjunction with the accompanying drawings.

DETAILED DESCRIPTION OF THE PREFERRED EMBODIMENT

Figure 1:
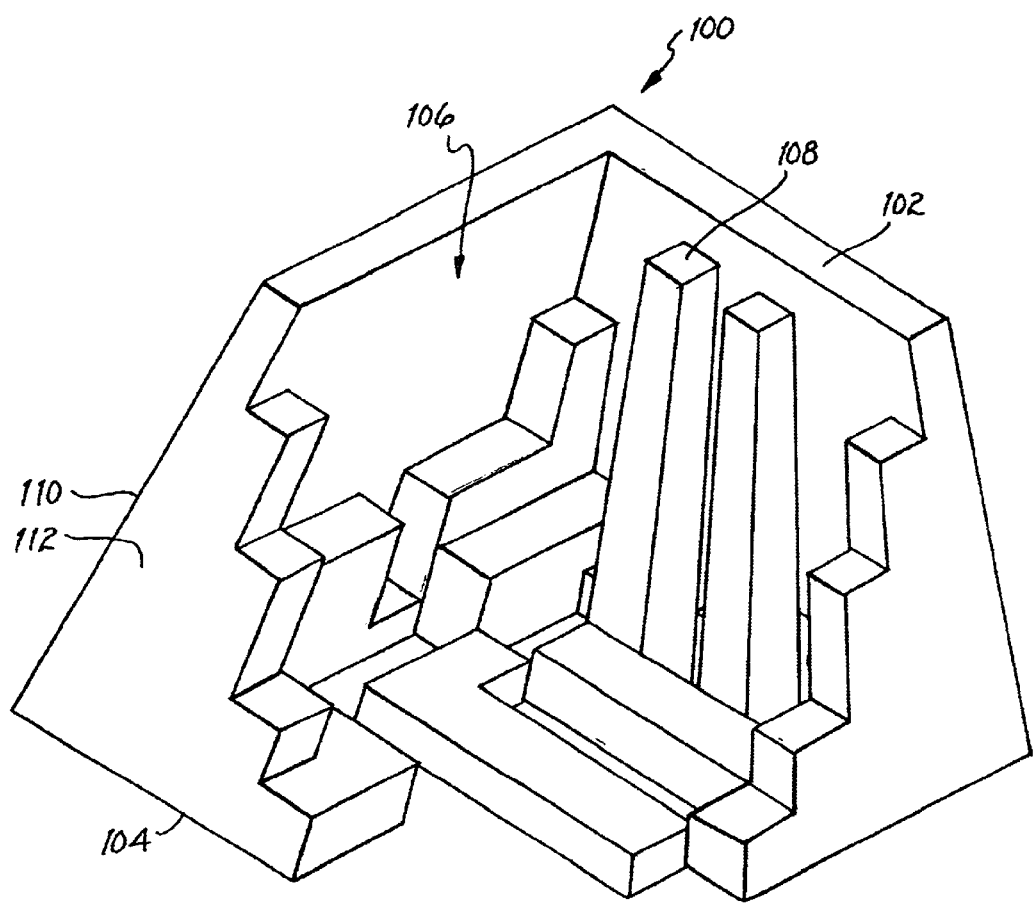
FIG. 1 is an elevated perspective view of a prior art radiation modulating device.

Referring to FIG. 1, a prior art radiation modulating device 100 is shown. The radiation modulating device 100 has a housing 110 and a core area 106. The housing 110 includes a top 102, a bottom 104, and side walls 112. The core area 106 has a plurality of segments 108 generally configured to partially or completely block one or more portions of a radiation beam.

Figure 2:
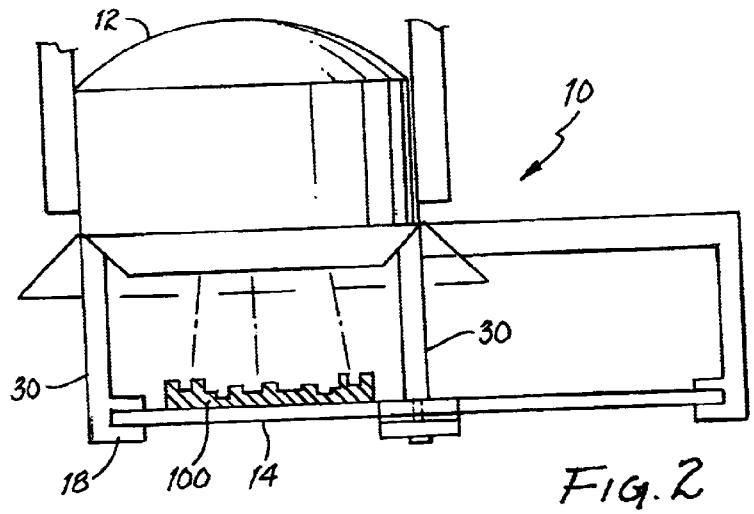
FIG. 2 is a side view of one embodiment of an apparatus which is coupled to a radiation device which will allow the radiation device to alter the amount of radiation delivered to the body.

As stated above, a problem exist in that one has to frequently change out the radiation modulating device 100 between the radiation source and the target area. This generally is fairly time consuming and causes too much treatment down time. Thus, referring now to FIGS. 2–4, an apparatus 10 which is coupled to a radiation device 12 which will allow the radiation device 12 to alter the amount of radiation delivered to a treatment area is shown.

The apparatus 10 has a plate member 14. In the Figures, the plate member 14 is circular in shape. However, this is just given as an example and should not be seen as to limit the scope of the present invention. The plate member 14 will have a plurality of openings 16 located thereon. Each opening 16 is used to house and hold a radiation modulating device 100. As may be seen most clearly in FIG. 3, the openings 16 are located around the periphery of the plate member 14. The plate member 14 is of a sufficient size to have a plurality of radiation modulating device 100 positioned around the periphery thereof.

The plate member 14 may have one or more handles 17. The handles 17 may be positioned anywhere on the plate member 14. In the embodiment depicted in FIG. 3, the handles 17 are located on the outer periphery of the plate member 14. However, this should not be seen as to limit the scope of the present invention. The handles 17 are provided to allow one to hold and move the plate member 14.

Figure 3:
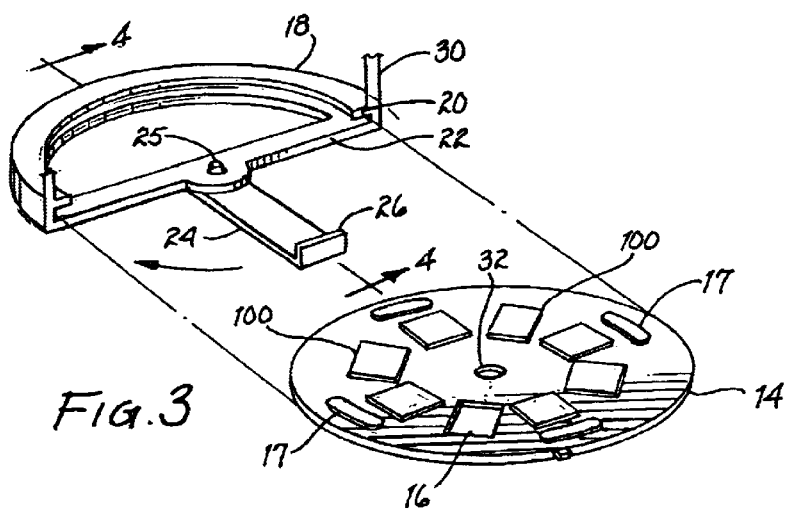
FIG. 3 is an elevated perspective view of the apparatus depicted in FIG. 2.
Figure 4:
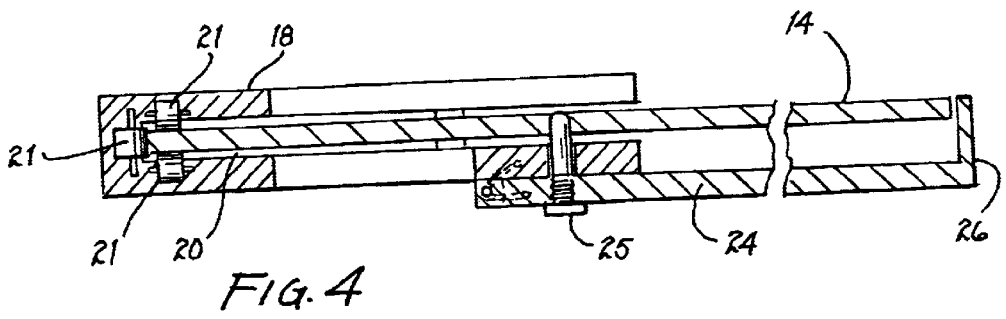
FIG. 4 is a cross-sectional side view taken along lines 4—4 of FIG. 3 of the apparatus depicted in FIG. 2

The apparatus 10 has a frame member 18. The frame member 18 is similar in shape to the plate member 14. As shown in FIG. 3, the frame member is semi-circular in shape. However, this should not be seen as to limit the scope of the present invention. The frame member 14 just has to be able to support the plate member 18 in a horizontal position.

In the embodiment depicted in the Figures, the frame member 18 fits around approximately half of the outer perimeter of the plate member 14. A channeling 20 runs along an inner circumference of the frame member 18. When the frame member 18 is used to support and hold the plate member 14, the plate member 14 will slide into the channeling 20. Thus, the channeling 20 is also used to support and hold the plate member 14 within the frame member 18.

Located within the channeling 20 is a plurality of rollers 21. As may be seen more clearly in FIG. 4, the rollers 21 may be located on a top surface, a bottom surface, and/or a side surface of the channeling 20. The rollers 21 are used to rotate the plate member 14 within the channeling 20. In general, the rollers 21 will have a rubberized surface in order to grip and rotate the plate member 14. However, this should not be seen as to limit the scope of the present invention. Any type of rollers 21 may be used as long as the rollers 21 are able to rotate the plate member 14 within the channeling 20.

The rollers 21 may be coupled to a control mechanism. The control mechanism may be a computer or the like. The control mechanism is used to control the movement of the rollers 21. By controlling the movement of the rollers 21, one can rotate the plate member 14 within the channeling 20. Alternatively, one can manually rotate the plate member 14 within the channeling 20.

The frame member 18 has a cross bar 22. The cross bar 22 runs from a first end of the frame member 18 to a second end of the frame member 18. The cross bar 22 is used to provide additional support for the frame member 18 so that the frame member 18 can hold and support the plate member 14.

A rotatable arm 24 is coupled to the cross bar 22. The rotatable arm 24 is rotatably coupled to a cental area of the cross bar 22 by a peg member 25. The rotatable arm 24 will rotate about the peg member 25 in either a clockwise or counter-clockwise fashion. The rotatable arm 24 is also used to support and hold the plate member 14 in the frame member 18. Located on one end of the rotatable arm 24 is a raised member 26. The raised member 26 is perpendicular to the rotatable arm 24. The raised member 26 is used to secure the plate member 14 within the frame member 18 so that the plate member 14 is free to rotate within the frame member 18 but cannot be removed without rotating the rotatable arm 24 to an open position.

A pair of arms 30 extend up from each end of the frame member 18. The pair of arms 30 are used to secure the apparatus 10 to a radiation source 12.

Operation

In operation, the pair of arms 30 are used to secure the apparatus 10 to a radiation source 40. The rotatable arm 24 will be moved so that a plate member 14 may be inserted into the channeling 20 of the frame member 18. In order to proper align the plate member 14 within the frame member 18, an opening 32 may be formed within the center of the plate member 14. The opening 32 is then positioned over the peg member 25 to ensure that the plate member 14 is proper aligned within the frame member 18.

Once the plate member 14 is positioned in the channeling 20 of the frame member 18, the rotatable arm 24 is moved so that the rotatable arm 24 is perpendicular to the cross bar 22. This will lock the plate member 14 within the frame member 18. The plate member 14 is then rotated either by a control mechanism or by hand so that the proper radiation modulating device 100 is in position directly below the radiation beam. The plate member 14 can be rotated so that different radiation modulating device 100 may be used to provide different levels of radiation treatment.

While the invention has been particularly shown and described with reference to preferred embodiments thereof, it will be understood by those skilled in the art that the foregoing and other changes in form and details may be made therein without departing from the spirit and scope of the invention.

What is claimed is:

1. An apparatus for altering the radiation intensity delivered from a radiation source to a patient for medical treatment of the patient comprising, in combination:
    a plate member for holding a plurality of radiation modulating devices used for radiation treatment of the patient; and
    a frame member coupled to the radiation source for holding and locking the plate member, the frame member allowing the plate member to be positioned between the radiation source and a target area of the patient wherein the frame member allows the plate member to rotate within the frame member so different radiation modulating devices may be positioned between the radiation source and the target area of the patient to alter the radiation intensity delivered to the patient for medical treatment.

2. An apparatus for altering the radiation intensity delivered from a radiation source in accordance with claim 1 wherein the plate member comprises a plurality of openings formed around the periphery of the plate member for holding the plurality of radiation modulating devices.

3. An apparatus for altering the radiation intensity delivered from a radiation source in accordance with claim 1 wherein the plate member comprises at least one handle formed on the plate member.

4. An apparatus for altering the radiation intensity delivered from a radiation source in accordance with claim 1 wherein in the frame member comprises:
    a housing which is positioned around a section of the plate member when the plate member is placed within the frame member;
    a channeling which runs along a length of the housing;
    a cross bar member coupled between a first end and a second end of the housing; and
    a pair of support arms coupled to the housing for coupling the frame member to the radiation source.

5. An apparatus for altering the radiation intensity delivered from a radiation source in accordance with claim 4 wherein the frame member further comprises a rotatable arm member rotatably coupled to the cross bar for securing the plate member within the frame member.

6. An apparatus for altering the radiation intensity delivered from a radiation source in accordance with claim 5 wherein the rotatable arm member has a raised member coupled to an end of the rotatable arm.

7. An apparatus for altering the radiation intensity delivered from a radiation source in accordance with claim 4 wherein the frame member further comprises a plurality of rollers located within the channeling for rotating the plate member within the channeling.

8. An apparatus for altering the radiation intensity delivered from a radiation source comprising, in combination:
    a plate member having a plurality of openings formed around the periphery of the plate member for holding a plurality of radiation modulating devices; and
    a frame member coupled to the radiation source for holding the plate member between the radiation source and a target area wherein the frame member allows the plate member to rotate within the frame member so different radiation modulating devices may be positioned between the radiation source and the target area to alter the radiation intensity delivered wherein the frame member comprises:
        a housing which is positioned around a section of the plate member when the plate member is placed within the frame member;
        a channeling which runs along a length of the housing;
        a cross bar member coupled between a first end and a second end of the housing;
        a pair of support arms coupled to the housing for coupling the frame member to the radiation source; and
        a rotatable arm member rotatable coupled to the cross bar for securing the plate member within the frame member.

9. An apparatus for altering the radiation intensity delivered from a radiation source in accordance with claim 8 wherein the plate member further comprises at least one handle formed on the plate member.

10. An apparatus for altering the radiation intensity delivered from a radiation source in accordance with claim 8 wherein the rotatable arm member has a raised member coupled to an end of the rotatable arm.

11. An apparatus for altering the radiation intensity delivered from a radiation source in accordance with claim 8 wherein the frame member further comprises a plurality of rollers located within the channeling for rotating the plate member within the channeling.

* * * * *